(12) United States Patent
Cleveland

(10) Patent No.: US 6,598,971 B2
(45) Date of Patent: Jul. 29, 2003

(54) METHOD AND SYSTEM FOR ACCOMMODATING PUPIL NON-CONCENTRICITY IN EYETRACKER SYSTEMS

(75) Inventor: Dixon Cleveland, Annandale, VA (US)

(73) Assignee: LC Technologies, Inc., Fairfax, VA (US)

( * ) Notice: Subject to any disclaimer, the term of this patent is extended or adjusted under 35 U.S.C. 154(b) by 0 days.

(21) Appl. No.: 09/986,368

(22) Filed: Nov. 8, 2001

(65) Prior Publication Data

US 2003/0086057 A1 May 8, 2003

(51) Int. Cl.[7] ................................. A61B 3/14
(52) U.S. Cl. ..................................... 351/209
(58) Field of Search ..................... 351/204, 208, 351/209, 210, 221, 246; 348/16; 396/51

(56) References Cited

U.S. PATENT DOCUMENTS

| | | |
|---|---|---|
| 3,462,604 A | 8/1969 | Mason |
| 4,859,050 A * | 8/1989 | Borah et al. ............. 351/210 |
| 5,094,521 A | 3/1992 | Jolson et al. |
| 5,500,671 A | 3/1996 | Anderson et al. |
| 5,532,784 A | 7/1996 | Nishimura et al. |
| 5,861,940 A * | 1/1999 | Robinson et al. ............. 351/221 |

FOREIGN PATENT DOCUMENTS

WO        02/35219        11/2001

OTHER PUBLICATIONS

"Method and Designs, Survey of Eye Movement Recording Methods", by Laurence R. Young, Behavior Research Methods & Instrumentation 1975, vol. 7 (5), 397–429.

"A Remote Oculmeter Permitting Head Movement", by J. Merchant and R. Morrissette, Honeywell Radiation Center, 1973.

* cited by examiner

Primary Examiner—George Manuel
(74) Attorney, Agent, or Firm—Shaw Pittman LLP

(57) ABSTRACT

Embodiments of the present invention relate to eyetracking methods and systems that compensate for physiological variations in the location of the pupil within the eye. In one embodiment, a video eyetracker measures the location of a pupil within the eye. Using measured observable features of the eye, including pupil diameter, a pupil-location-offset is estimated with respect to a fixed point on the eyeball. The location of a fixed point within the eyeball is estimated as a function of the measured pupil location and the estimated pupil-location-offset.

44 Claims, 3 Drawing Sheets

CAMERA IMAGE OF EYE, ILLUSTRATING
BRIGHT IMAGE PUPIL AND CORNEAL REFLECTION

PUPIL CENTER SHIFT AS A FUNCTION
OF PUPIL DIAMETER - PHYSIOLOGICAL REPRESENTATION

PUPIL CENTER SHIFT AS A FUNCTION
OF PUPIL DIAMETER - GRAPHICAL REPRESENTATION
(WITHOUT HYSTERESIS)

EXAMPLE OF PUPIL CENTER HYSTERESIS

EXAMPLE LIGHT LEVEL PROFILE TO INDUCE PUPIL CHANGE AND AID IN THE MEASUREMENT OF PUPIL-CENTER HYSTERESIS THROUGHOUT THE HYSTERESIS ENVELOPE

METHOD AND SYSTEM FOR ACCOMMODATING PUPIL NON-CONCENTRICITY IN EYETRACKER SYSTEMS

BACKGROUND OF INVENTION

1. Field of Invention

Embodiments of the present invention relate to eyetracking systems and methods that compensate for physiological variations in the location of the pupil within the eye.

2. Background Information

Eyetracking has application in many areas of technology, including software applications used to assist those with disabilities, military uses, and space programs. Generally, eyetracking has application in any system where it is desired to know where a user is looking.

In known video eyetracking methods, the angular orientation, or gaze direction, of the eye is measured via analysis of an image of the eye. Typically, the image is made with a camera. Referring to FIG. 1, a video camera 4 observes an observer's eye 1, which is illuminated by a light source 3. The light source 3 (e.g., an infrared light-emitting diode) illuminates the eye 1 as the viewer looks at a screen 2. FIG. 2 illustrates an example of an image of the eye 1 as seen by a camera. The resulting camera image of the eye 1 includes the iris, the pupil 5 (with a center 10) and a corneal reflection 6, i.e., a reflection of the light source off the reflective corneal surface of the eye.

Given that the cornea is approximately spherical in shape, the corneal reflection moves continuously across the eye as the eye changes its orientation. Using the Pupil Center Corneal Reflection (PCCR) method, as disclosed in the references U.S. Pat. No. 3,462,604 to K. Mason, Control Apparatus Sensitive to Eye Movement; John Merchant & Richard Morrissette, *A Remote Oculometer Permitting Head Movement*, Report No. AMRL-TR-73-69 (Honeywell Radiation Center 1973); and Laurence R. Young & David Sheena, *Methods & Designs: Survey of Eye Movement Recording Methods*, Behavior Research Methods & Instrumentation, Vol. 7(5), 397–429 (1975), the eye's orientation is determined from the relative locations of the pupil center 10 and the corneal reflection 6 within the camera image (see FIG. 2). It is known that the vertical and horizontal orientation of the eye is directly related to the vector distance between the corneal reflection 6 and the pupil center 10. For example, as the eye rotates upward, the pupil 5 (and thus the pupil center 10) moves upward with respect to the corneal reflection 6, and as the eyeball rotates toward the camera's right, the pupil center 10 moves right with respect to the corneal reflection image.

The corneal reflection is often referred to as the glint spot, and the vector between the glint spot and the pupil center is often referred to as the glint-pupil vector:

$$v_x = x_{pupil} - x_{glint} \tag{1a}$$

$$v_y = y_{pupil} - y_{glint} \tag{1b}$$

where:

$v_x$, $v_y$ are the horizontal and vertical components of the glint-pupil vector (input variable set)

$x_{pupil}$, $y_{pupil}$ are the x,y location of the pupil-center image within the camera frame $x_{glint}$, $y_{glint}$ are the x,y location of the corneal-reflection image within the camera frame.

Known eyetracker systems and methods commonly use mathematical equations to predict the eye orientation from the measured glint-pupil vector. A simple example of a known equation to predict the eye orientation is:

$$Theta_{horz} = A_{x0} + A_{x1} v_x \tag{2a}$$

$$Theta_{vert} = A_{y0} + A_{y1} v_y \tag{2b}$$

where:

$Theta_{horz}$, $Theta_{vert}$ are the horizontal and vertical angles of the eye orientation, and $A_{x0}$, $Ax_1$, $A_{y0}$, $A_{y1}$ are the coefficients used in predicting the eye's orientation (calibration parameter set).

The variables from which the eye orientation is computed are commonly referred to as the "input variable set". In the example of Equations 2a, 2b above, the input variable set consists of the variables ($v_x$ and $v_y$). The coefficients, used to compute the eye orientation from the input variable set, are often referred to as the "calibration parameter set". In the example of Equations 2a, 2b above, the calibration parameter set consists of the coefficients ($A_{x0}$, $Ax_1$, $A_{y0}$, and $A_{y1}$).

Typically, a "calibration procedure" is used to determine optimum values for calibration parameters. One known calibration procedure consists of the user fixating on a sequence of known locations. A set of "raw" data is collected at each calibration point, where the raw data consists of the known gaze directions and a set of measured input data for each of the calibration points. After the raw data for all the calibration points has been collected an optimization procedure, such as a regression analysis, is executed to find optimal values for the calibration parameters, which yield a minimum aggregate error in predicting the known gaze directions for all the calibration points.

Problem Predicting Gaze Direction Accurately

When using the PCCR method to measure the orientation of an eye, it is assumed that the pupil center represents a fixed point within the eyeball structure. A problem exists, however, in that as the iris dilates and constricts, the pupil typically does not open and close completely concentrically about a fixed point on the eye. An exaggerated example of an eye with pupil-center shift is illustrated in FIG. 3. FIG. 3 illustrates an example of how two pupils are not concentric; the two pupil centers (9, 10) are at different locations within the eye. Pupil center 9, the center point of pupil circumference 8 is offset from pupil center 10, the center point of pupil circumference 7.

This pupil center shift can be explained as follows: The iris contracts the dilates using two opposing muscles. The sphincter pupillae, oriented circumferentially around the inner edge of the iris, effects contraction by pulling the pupil closed. The dilator pupillae, oriented radially, effects dilation by pulling the pupil open. If the sphincter and/or dilator pupillae do not actuate symmetrically around the pupil, or if there is an imbalance in the counteracting push/pull mechanics of the iris's sphincter and dilator muscles, the pupil center shifts within the eyeball.

A problem exists because of the extent that the pupil-center location varies within an eyeball, the glint pupil vector (as measured within the camera image) will not represent a vector from the corneal reflection to a fixed point on the eyeball, and errors result in the calculation of the eyeball orientation, unless these pupil-center shifts are accommodated.

Typically, human pupils open and close concentrically enough to maintain PCCR eyetracking accuracies of approximately 0.7 degrees (using root mean square error measurement). However, a need exists for a more accurate method for cases where more accurate eyetracking is desired, or for people whose pupil center(s) shift more than normal within the eyeball(s). Accordingly, it is desirable to have methods to measure the image location of a more nearly fixed reference point within the eyeball.

SUMMARY OF THE INVENTION

Embodiments of the invention include a method of using a computer system to determine an eye's pupil-offset from a fixed location on the eyeball as a function of its diameter using an eyetracker system and the pupil-center-corneal reflection method to measure glint-pupil vectors of an observer's eye. Preferably, the observer fixates an eye on one or more given points on a screen and the system is used to measure at least one additional glint-pupil vector of the eye. The system quantifies measured variations in the glint-pupil vector as pupil offsets with respect to a fixed location on the eyeball and codifies them as a function of measured pupil diameters.

Additional embodiments of the invention include a method to determine the orientation of an eye by accommodating for the eye's pupil center shift, comprising the steps of determining the location of the pupil; measuring at least one observable feature of the eye related to the relative location of the pupil within the eyeball; estimating a pupil-location-offset parameter with respect to a fixed point on the eyeball using at least one said measured observable eye feature; and calculating the location of a fixed point within the eyeball as a function of the measured pupil location and the estimate of the pupil-location offset.

Other embodiments of the invention include a method of using a computer system to quantify an eye's pupil-offset behavior, comprising the steps of using an eyetracker system and the pupil-center-corneal reflection method to measure a first glint-pupil vector of the eye; fixating the eye on one or more given points on a screen; measuring at least one additional glint-pupil vector of the eye; and quantifying measured pupil offsets as functions of measured pupil diameters.

Still other embodiments of the invention include a system for compensating for pupil non-concentricity in an eye-tracker system, comprising a video eyetracker for tracking the position of an observer's eye; a processor for using the pupil-center-corneal reflection method to measure at least one glint-pupil vector; a means for measuring glint-pupil vectors as the pupil diameter varies; and a processor for interpreting the measured variations in the glint-pupil vector as pupil offsets with respect to a fixed location on the observer's eyeball and codified as a function of the measured pupil diameters.

Embodiments of the invention also include an apparatus for estimating the gaze direction of an eye comprising a computer and a camera for observing the eye. A measuring means measures pupil diameter and features of the eye related to the relative location of the pupil within the eyeball and a processor estimates the pupil-location-offset with respect to a fixed point on the eyeball using at least one of the measured observable eye features. A processor estimates the location of the fixed point within the eyeball as a function of the measured pupil location and the estimate of the pupil-location offset.

DETAILED DESCRIPTION

One method for determining the location of a fixed reference point within the eyeball is to measure the iris/sclera boundary, which is physically more stable than the pupil/iris boundary. In some lighting conditions, however, the iris/sclera boundary can be difficult to measure accurately, and the eyelids usually obscure much of the upper and lower parts of this boundary, so it can be difficult to measure its center point accurately from the observable points of the iris/sclera boundary. Another method for determining the location of a fixed reference point within the eyeball is to recognize and locate a visible landmark on the eyeball surface, such as a blood vessel in the sclera, a distinguishing feature of the iris/pupil boundary, or a distinguishing landmark of the iris fiber pattern toward the outer edge of the iris.

According to an embodiment of the present invention, a novel method for measuring a more nearly fixed reference point within the eyeball comprises steps for adjusting the measured pupil-center location based on any known dependencies of the pupil-center location on measurable pupil features. For most eyes, the iris's physiological behavior typically follows repeatable patterns as it dilates and constricts. Thus, shifting of the pupil center with respect to a fixed reference point within the eyeball is not random. Accordingly, much of any pupil-location shifting can be predicted by observing the behavior of the pupil diameter. According to methods of the present invention, if a measurement of the present pupil location within the camera image is known and an estimate of the pupil-center shift with respect to a fixed reference point on the eyeball can be made, the location of a fixed eyeball reference point can be estimated within the camera image. According to one embodiment of the present invention, the effect of pupil-center shift is accommodated by computing an "adjusted pupil location" within the camera image, where the adjusted pupil location is taken to be the location of the true (i.e., measured) pupil center and the estimated pupil-center shift from a fixed reference point. The location of the fixed reference point is arbitrary, but is often defined to be the point where the optic axis of the eye intersects the corneal surface.

Finally, according to one exemplary embodiment of the present invention, to predict the eyeball's orientation more accurately, an "adjusted" or "corrected" glint-pupil vector is defined to be the vector distance from the corneal reflection to the estimated fixed reference point on the eyeball.

Mathematical Representation of Pupil-Center-Shift vs Pupil Diameter

Figure 1:
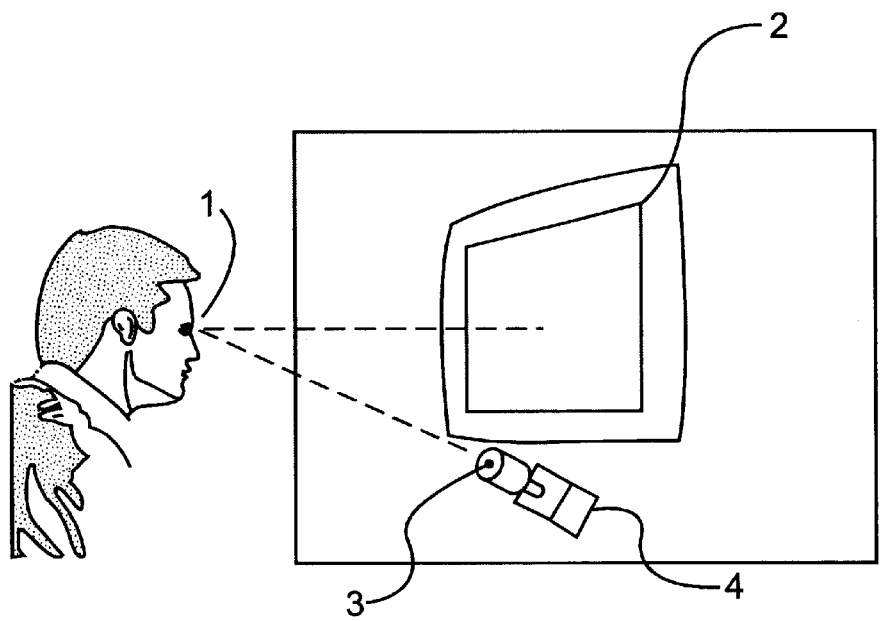
FIG. 1 shows an illustration of known video eyetracker systems.
Figure 2:
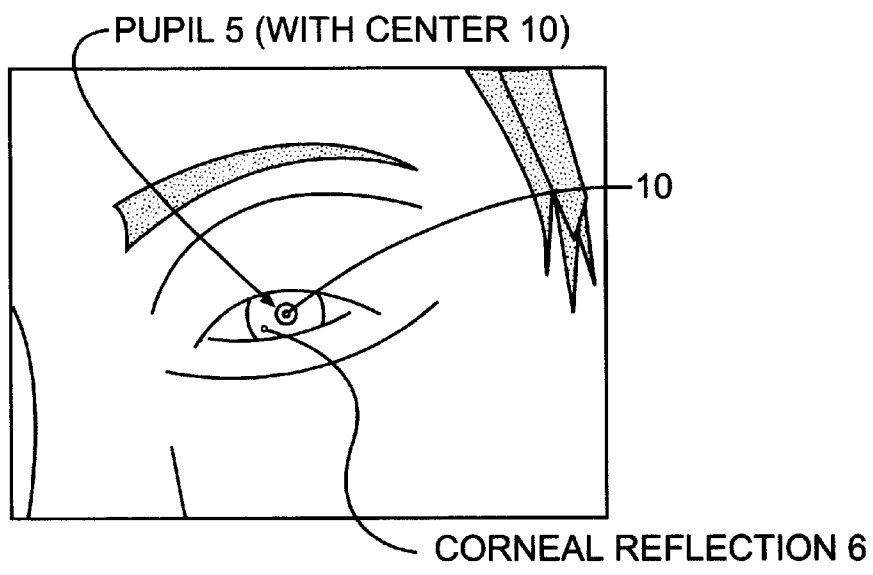
FIG. 2 shows an example of a camera image of an eye exhibiting a bright image pupil and a corneal reflection.
Figure 3:
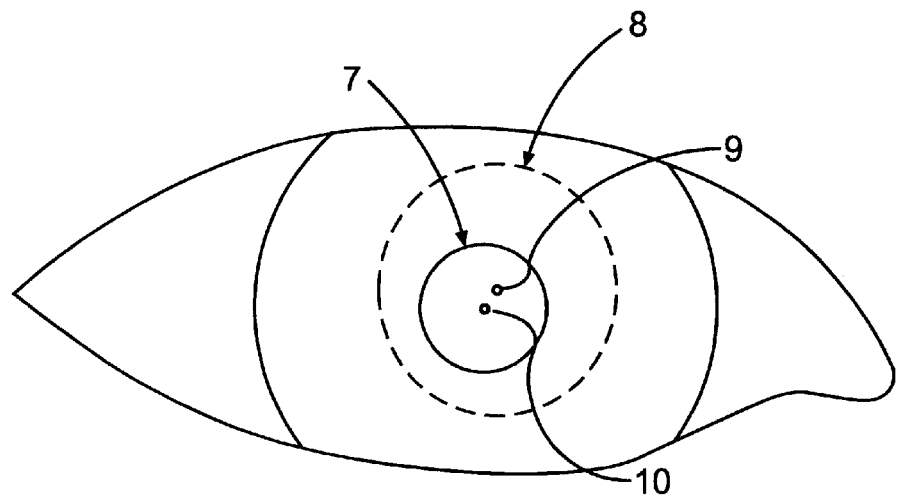
FIG. 3 illustrates an example of pupil center shift as a function of pupil size.
Figure 4:
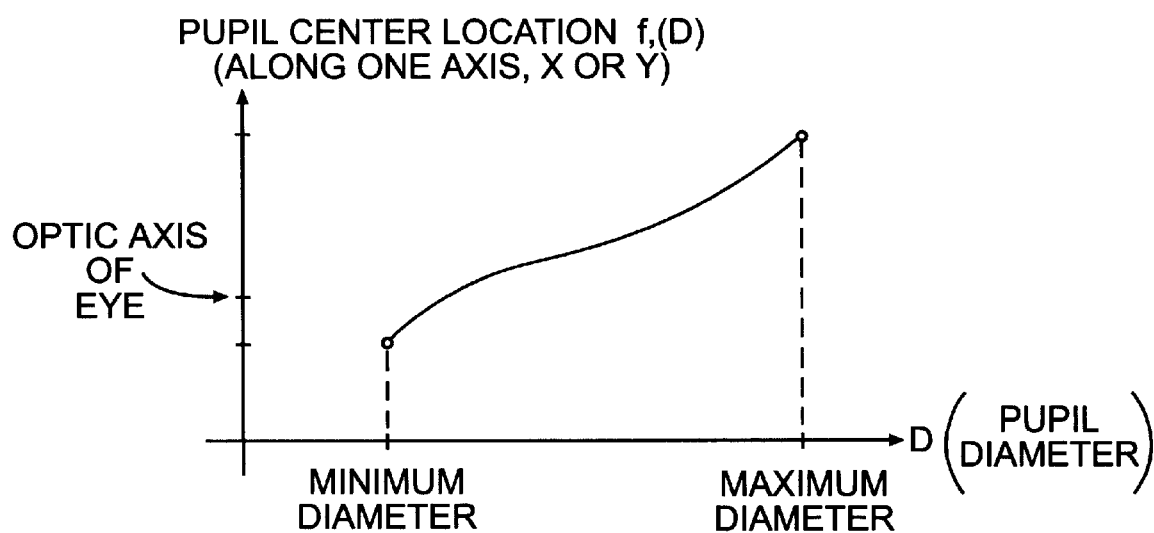
FIG. 4 illustrates a graphical representation of pupil center shift as a function of pupil diameter without hysteresis.

FIG. 4 shows an example of a graphical representation of pupil-center shift as a function of pupil diameter for a full range of pupil diameter $D_{pup}$. (Note: two such curves exist for each eye, each representing different dimensions of the eye's two-dimensional pupillary surface.) For this example, $f_x(D_{pup})$ and $f_y(D_{pup})$ represent the horizontal and vertical behaviors of the pupil-center location, wherein:

$$x_{pup\text{-}offset} = f_x(D_{pup}) \qquad (3a)$$

$$y_{pup\text{-}offset} = f_y(D_{pup}) \qquad (3b)$$

where:

$x_{pup\text{-}offset}$, $x_{pup\text{-}offset}$ are the estimates of the horizontal and vetical components of the pupil center offset with respect to a fixed reference point on the eyeball;

$D_{pup}$ is the measured pupil diameter (pupil-offset feature); and $f_x(D_{pup})$, $f_y(D_{pup})$ are functions which predict the horizontal and vertical components of pupil-offset as a function of pupil diameter.

Mathematical representations of the pupil-center shift may be expressed in terms of equations or tables. As a simple example, the pupil-location offsets may be approximated by a pair of linear equations:

$$f_x(D_{pup}) = x_{nom\text{-}offset} + K_x(D_{pup} - D_{nom}) \qquad (4a)$$

$$f_y(D_{pup}) = y_{nom\text{-}offset} + K_y(D_{pup} - D_{nom}) \qquad (4b)$$

where:

$D_{nom}$ is a constant representing a "nominal" pupil diameter $x_{nom\text{-}offset}$, $y_{nom\text{-}offset}$ are constants representing the pupil-center offset given the nominal value of the pupil diameter $K_x$, $K_y$ are coefficients relating the change in the pupil-center offset as a function of the difference between the measured pupil diameter and the nominal pupil diameter In this linear example, parameters defining the pupil-center shift for an eye comprise the set ($D_{nom}$, $x_{nom\text{-}offset}$, $y_{nom\text{-}offset}$, $K_x$, $K_y$), and the input variable set determining the pupil offset at any time consists of the single variable $D_{pup}$, the pupil diameter at that time.

In other embodiments of the present invention, more complex functions relating pupil diameter to pupil-location offset may be used to generate more accurate models of the pupil behavior.

Pupil-Center Hysteresis

Referring to FIG. 4, the pupil-center offset (for the associated pupillary dimension) is shown as a single-valued function of the pupil diameter, i.e., it is assumed that there is a unique value for the pupil offset for any given value of the pupil diameter. This single-valued function represents no hysteresis in the pupil-center behavior.

In the more general case, however, pupil locations exhibit the phenomenon of hysteresis. For any given value of pupil diameter, the pupil offset may reside over a range of offsets. With hysteresis, the instantaneous value of the pupil center depends on the prior history of the pupil diameter, and on the direction that the pupil diameter was moving.

Figure 5:
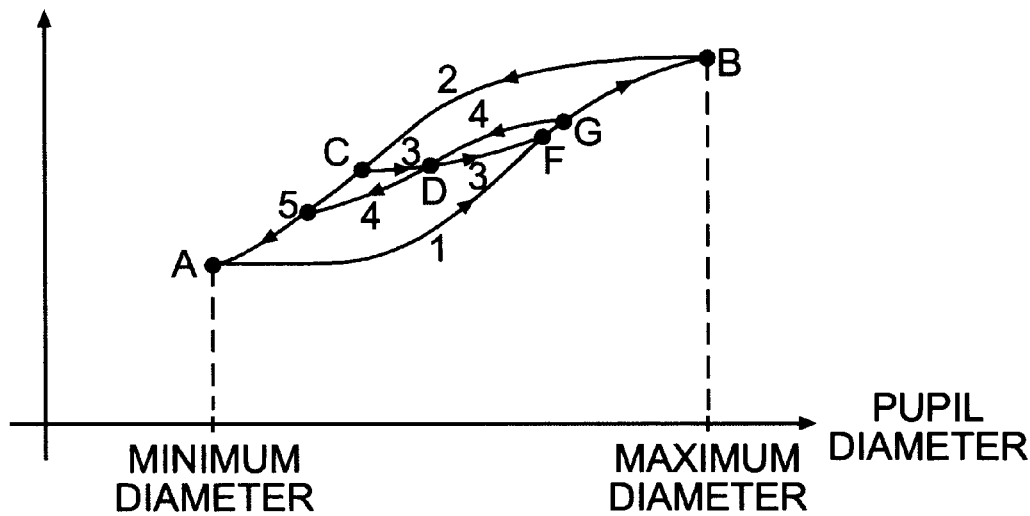
FIG. 5 illustrates a graphical representation of pupil-center hysteresis.

FIG. 5 illustrates an example of hysteresis in the pupil location as a function of pupil diameter. If the eye begins at its minimum pupil diameter, indicated by Point A in FIG. 5, the pupil center moves along Path 1 as the pupil diameter increases. If the pupil diameter continually opens to its maximum diameter, the pupil center follows Path 1 until it reaches Point B. As the pupil diameter closes from Point B, the pupil center follows Path 2, and remains on Path 2 all the way back to Point A, as long as the diameter closes monotonically, i.e., as long as the pupil diameter does not temporarily open by any amount along the way. Paths 1 and 2 are referred to as the envelope of the hysteresis loop, and Paths 1 and 2 define the minimum and maximum values of the pupil-center location as a function of the pupil diameter.

If the pupil diameter is closing along Path 2, and reverses its direction, when it reaches Point C for example, the pupil then transitions to Path 3, rather than retracing its path along 2. When it reaches Point D, the pupil can follow one of two paths. If the pupil continues to open, it continues to follow Path 3. If, on the other hand, the pupil diameter reverses direction and starts to close, the pupil switches to Path 4, not Path 3 that it came in on. Point D illustrates the general case within a hysteresis loop. If the pupil diameter is increasing, the pupil passes through the point on one path. If the diameter is decreasing, it moves through the point on another path. If the diameter switches direction at the point, the pupil switches paths.

Modeling Pupil Hysteresis

Pupil hysteresis may be modeled mathematically by defining a "pupil-offset hysteresis model" for the eye from which the pupil-center location may be tracked from observation of the pupil diameter history. The pupil-offset hysteresis model consists of mathematical expressions, which define how the pupil offset varies as a function of pupil-diameter changes, given all possible combinations of pupil diameter and pupil offset. To represent hysteresis, two separate expressions are defined for the pupil-offset versus pupil-diameter variation for the two cases where the pupil diameter is increasing and decreasing. Furthermore, since the pupillary surface is 2-dimensional, there are separate sets of rules for each axis of the pupil-center offset. The rules may be expressed, for example, in equation or table form.

Mathematically, the two pupil-offset versus pupil-diameter variations are expressed as derivatives of the pupil offset as a function of increasing or decreasing pupil diameter:

$$dx_{pup\text{-}offset}/dD_{pup}(D_{pup}, x_{pup\text{-}offset}, \text{ increasing}) \text{ and} \qquad (5a)$$

$$dx_{pup\text{-}offset}/dD_{pup}(D_{pup}, x_{pup\text{-}offset}, \text{decreasing}) \qquad (5a)$$

Note that there is a corresponding pair of expressions for the pupil's vertical axis:

$$dy_{pup\text{-}offset}/dD_{pup}(D_{pup}, y_{pup\text{-}offset}, \text{increasing}) \text{and} \qquad (5c)$$

$$dy_{pup\text{-}offset}/dD_{pup}(D_{pup}, y_{pup\text{-}offset}, \text{decreasing}) \qquad (5d)$$

These four derivatives express the change in pupil offset with respect to the change in pupil diameter as a function of the diameter direction of change, and thus represent the two different "path directions" discussed above. The arguments $D_{pup}$, $y_{pup\text{-}offset}$ and $y_{pup\text{-}offset}$ indicate that the values of the derivatives vary according to the current values of those variables. The arguments "increasing" or "decreasing" indicate which curve to use, depending on whether the pupil diameter is increasing or decreasing.

Procedure for Estimating Pupil-Center Offset from the Pupil-Offset Hysteresis Model Below, an example of a preferred embodiment of the present invention for estimating pupil-center offset is discussed. During an eyetracking operation, the pupil-center offset may be predicted by the following illustrative iterative procedure:

1) First, record or recall a prior measured pupil diameter $D_{past}$ and the previously predicted pupil offset $x_{pup\text{-}offset\text{-}past}$ and $y_{pup\text{-}offset\text{-}past}$.

2) Measure the present pupil diameter $D_{pres}$.

3) Determine the change in pupil diameter $dD_{pup}$:

$$dD_{pup} = D_{pres} - D_{past} \qquad (6)$$

and determine whether the pupil diameter increased or decreased.

4) Find the appropriate values for $dx_{pup\text{-}offset}/dD_{pup}$ and $dy_{pup\text{-}offset}/dD_{pup}$ from a pupil-offset hysteresis model based on:

pupil-diameter increase or decrease, the past pupil diameter $D_{past}$, and the past pupil offset $x_{past}$ and $y_{past}$.

5) Compute the changes in pupil offset $dx_{pup\text{-}offset}$ and $dy_{pup\text{-}offset}$ as a function of the change in pupil diameter. If the pupil diameter is increasing:

$$dx_{pup\text{-}offset} = dx_{pup\text{-}offset}/dD_{pup}(D_{pup}, x, \text{increasing}) * dD_{pup} \quad (7a)$$

$$dy_{pup\text{-}offset} = dy_{pup\text{-}offset}/dD_{pup}(D_{pup}, y, \text{increasing}) * dD_{pup} \quad (7b)$$

Otherwise, if the pupil diameter is decreasing:

$$dx_{pup\text{-}offset} = dx_{pup\text{-}offset}/dD_{pup}(D_{pup}, x, \text{decreasing}) * dD_{pup} \quad (8a)$$

$$dy_{pup\text{-}offset} = dy_{pup\text{-}offset}/dD_{pup}(D_{pup}, y, \text{decreasing}) * dD_{pup} \quad (8b)$$

(Note: In the case that the pupil diameter does not change, $dD_{pup}$ is zero, so it does not matter whether the "increasing" or "decreasing" expressions are used. In this case, $dx_{pup\text{-}offset}$ and $dy_{pup\text{-}offset}$ will be zero, whether computed by either Equations 7a, 7b or 8a, 8b).

6) Compute the new pupil offset from the old pupil offset and the change in the pupil offset:

$$x_{pup\text{-}offset} = x_{pup\text{-}offset\text{-}past} + dx_{pup\text{-}offset} \quad (9a)$$

$$y_{pup\text{-}offset} = y_{pup\text{-}offset\text{-}past} + dy_{pup\text{-}offset} \quad (9b)$$

Note: Preferably, if the change in pupil diameter $dD_{pup}$ is large enough that there is significant curvature along the path from $D_{past}$ to $D_{pres}$, the pupil diameter change should be broken into smaller segments and steps (a) through (f) repeated for each segment.

Method for Accommodating Pupil-Center Shift

The implementation of a preferred procedure for estimating the location of a fixed reference point within the eyeball structure consists of the following steps:

First, the location of the pupil is measured within the eye image. In video eyetracking, for example, the pupil center is often located by measuring points around the edge of the pupil, fitting an ellipse to these edge points, and mathematically calculating the center point of the ellipse. (Typically, the "pupil location" is taken to be the center point of the pupil, but other pupil location metrics, e.g. the bottom-most point on the pupil, may be used.)

Next, observable features of the eye are measured, including, for example, pupil diameter, which are related to the relative location of the pupil within the eyeball. Video eyetrackers typically measure pupil diameter as part of their routine image processing procedures. For example, the above-described elliptical fit procedure for locating the pupil center also produces a pupil diameter measurement. Additional parameters, such as the time derivative of pupil diameter, may also be used to support the estimation of pupil-center offset.

Using the measured observable eye feature, the pupil-location offset is estimated with respect to fixed reference point on the eyeball. An example method for estimating the pupil-location offset based on measured pupil-offset features of the pupil (without hysteresis) was given in equations 3 and 4 above. An example method for estimating the pupil-location offset based on measured pupil-offset features of the pupil (with hysteresis) was given in the above section entitled "Procedure for Estimating Pupil-Center Offset from the Pupil-Offset Hysteresis Model."

Next, the location of the fixed reference point within the eyeball is estimated as a function of the measured pupil location and the estimate of the pupil-location offset. Typically, the location of the fixed reference point within the eyeball is expressed as the sum of the pupil location and the pupil-location offset:

$$x_{fixed\text{-}ref\text{-}pt} = x_{pup\text{-}loc} + x_{pup\text{-}offset} \quad (10a)$$

$$y_{fixed\text{-}ref\text{-}pt} = y_{pup\text{-}loc} + y_{pup\text{-}offset} \quad (10b)$$

where:

$x_{fixed\text{-}ref\text{-}pt}$, $y_{fixed\text{-}ref\text{-}pt}$ represent the estimated location, within the camera image, of the fixed reference point within the eyeball $x_{pup\text{-}loc}$, $x_{pup\text{-}loc}$ represent the location of the pupil within the camera image Determining an Eye's Pupil-Offset vs Diameter Curves The pupil-offset behavior of a given eye may be established by asking a user to fixate on one or more given points, and recording the measured variations in the glint-pupil vector as the pupil diameter varies. If the eye's position and orientation remain fixed with respect to the camera, the location of the corneal reflection off the eye remains fixed, and all variations in the glint-pupil vector within the camera image may be attributed to shifts in the pupil location.

To accommodate pupil-offset models without hysteresis, the pupil-offset functions for the eye may be determined by codifying the measured pupil offsets $f_x(D_{pup})$ and $f_y(D_{pup})$ as functions of the measured pupil diameters.

To accommodate pupil-center hysteresis and codify the $dx_{pup\text{-}offset}/dD_{pup}$ and $dy_{pup\text{-}offset}/dD_{pup}$ expressions for the pupil-diameter-increasing and pupil-diameter-decreasing paths, it is necessary to monitor and record pupil-center offset changes $dx_{pup\text{-}offset}$ and $dy_{pup\text{-}offset}$, pupil-diameter changes $dD_{pup}$, and whether the pupil diameter is increasing or decreasing.

Once pupil-offset data has been measured and recorded, standard modeling and curve-fitting tools may be used to generate expressions for $f_x(D_{pup})$ and $f_y(D_{pup})$ (for non-hysteresis models) and of $dx_{pup\text{-}offset}/dD_{pup}$ and $dy_{pup\text{-}offset}/dD_{pup}$ (for hysteresis models). Due to eyetracker instrumentation noise, for example, it may be necessary to measure the pupil-offset behavior multiple times to form good estimates of the pupil-offset functions.

Inducing Pupil Diameter Changes for Developing Pupil-Offset Models

To obtain a full representation of the eye's pupil-offset curve, it may be desirable to induce the pupil to move through its full range of expected diameters. The pupil diameter may be induced to open and close by varying the light levels of the object being fixated and/or varying the light levels of the background surrounding the object. To evoke smaller pupil diameters, calibration points may be taken with a relatively bright environment, and, to evoke larger pupil diameters, other calibration points may be taken with darker environments.

To obtain complete expressions for pupil location hysteresis throughout the hysteresis envelope, light levels may be modulated. For example, a light level may be shifted up and down gradually from several different light levels. A wide variety of intensity variation patterns can be used to induce and measure the hysteresis behavior of an eye's pupil-center offset. Preferably, to map the full hysteresis loop adequately, both the outside envelope of the loop and the opposing path directions within the loop are characterized.

Figure 6:
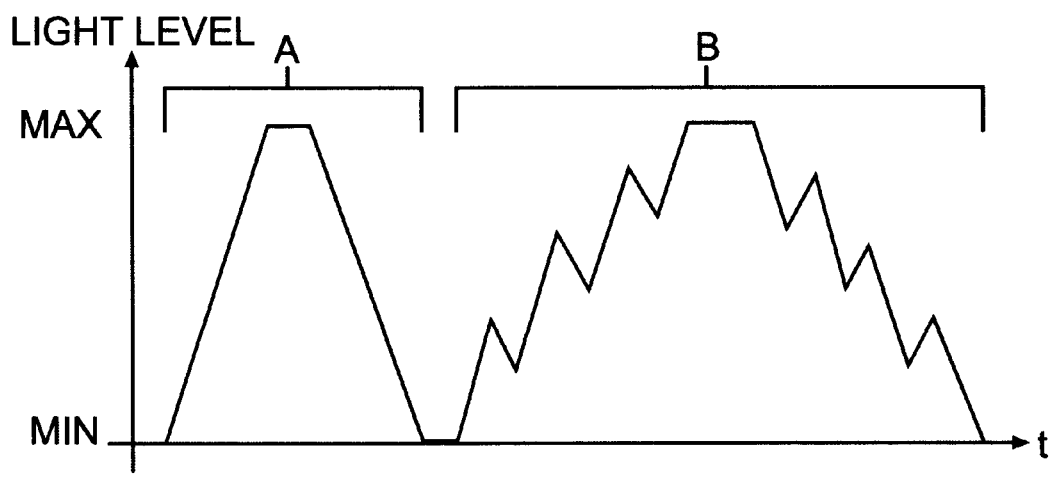
FIG. 6 illustrates a graphical representation of a light level profile, which can be used to induce pupil diameter changes and thus aid in the measurement of pupil-center hysteresis.

FIG. 6 depicts examples of light-level profiles that can be used to induce and measure the hysteresis behavior of an eye's pupil-center offset. In Section A the light level is monotonically increased from the lowest to the highest brightness level and then monotonically decreased from the highest to the lowest brightness level. These two "full-swing" light-level excitations induce the pupil behavior required to map the lower and upper contours of the outside envelope of the hysteresis loop. In Section B, another example shows how the light level is "saw toothed" up and down while gradually increasing and decreasing the overall light level. These reversing, saw-tooth variations in light level induce the pupil behavior required to map opposing path-directions within the envelope.

For eyetracking applications where a user is looking at a computer screen, and where the calibration data points are displayed on the computer screen, varying light levels may be achieved by changing the background brightness of the computer display during the collection of the calibration data. To achieve large pupil diameters, for example, calibration points may be displayed against a black background, and to achieve small pupil diameters, calibration points may be displayed against a bright white background. Typically, the large and small pupil diameters obtained using fully black and fully bright-white backgrounds during calibration provide a full range of pupil diameters expected to be encountered during eyetracking operation after the calibration session.

In describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, unless that order is explicitly described as required by the description of the process in the specification. Otherwise, one skilled in the art can readily appreciate that the sequences may be varied and still remain within the spirit and scope of the present invention.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary sill in the art in light of the above disclosure. The scope of the invention is to be defined only by the claims appended hereto, and by their equivalents.

What is claimed is:

1. A method to determine the location of a fixed point within an eyeball comprising the following steps:
measuring the location of a pupil;
measuring at least one observable feature of the eye related to the relative location of the pupil within the eyeball;
estimating a pupil-location-offset with respect to the fixed point on the eyeball using the at least one measured observable eye feature; and
calculating the location of the fixed point within the eyeball as a function of the measured pupil location and the estimated pupil-location offset.

2. A method according to claim 1, wherein said step of measuring observable features of the eye includes the step of measuring the pupil diameter.

3. The method according to claim 2, comprising an eyetracker calibration procedure for use on a computer system wherein variations in a user's pupil diameter are stimulated by varying a light level in a viewed environment.

4. The method according to claim 2, comprising an eyetracker calibration procedure used in conjunction with a computer screen display wherein variations in the user's pupil diameter are stimulated by changing the brightness of the screen display.

5. A method according to claim 2, including the steps of:
determining a prior measured pupil diameter $D_{past}$ and the prior predicted pupil offset $x_{pup\text{-}offset\text{-}past}$ and $y_{pup\text{-}offset\text{-}past}$;
measuring the pupil diameter $D_{pres}$;
determining the change in pupil diameter $dD_{pup}$ with the following relationship: $dD_{pup}=D_{pres}-D_{past}$;
determining whether the pupil diameter increased or decreased;
finding appropriate values for $dx_{pup\text{-}offset}/dD_{pup}$ and $dy_{pup\text{-}offset}/dD_{pup}$ from the pupil offset hysteresis model based on at least one of the following:
pupil-diameter increase or decrease;
the past pupil diameter $D_{past}$, and
the past pupil offset $x_{past}$ and $y_{past}$;
computing changes in pupil offsets $dx_{pup\text{-}offset}$ and $dy_{pup\text{-}offset}$ as a function of the change in pupil diameter; and
computing a quantity for new pupil offset from the old pupil offset and the change in the pupil offset with the following relationships:

$$x_{pup\text{-}offset}=x_{pup\text{-}offset\text{-}past}+dx_{pup\text{-}offset}$$

$$y_{pup\text{-}offset}=y_{pup\text{-}offset\text{-}past}+dy_{pup\text{-}offset}.$$

6. The method according to claim 5, comprising the step of computing changes in in pupil offsets $dx_{pup\text{-}offset}$ and $dy_{pup\text{-}offset}$ as a function of a change in pupil diameter, including the following steps if the pupil diameter is increasing:

$$dx_{pup\text{-}offset}=dx_{pup\text{-}offset}/dD_{pup}(D_{pup},x,\text{increasing})*dD_{pup}$$

$$dy_{pup\text{-}offset}=dy_{pup\text{-}offset}/dD_{pup}(D_{pup},y,\text{increasing})*dD_{pup}$$

and including the following steps if the pupil diameter is increasing:

$$dx_{pup\text{-}offset}=dx_{pup\text{-}offset}/dD_{pup}(D_{pup},x,\text{decreasing})*dD_{pup}$$

$$dy_{pup\text{-}offset}=dy_{pup\text{-}offset}/dD_{pup}(D_{pup},y,\text{decreasing})*dD_{pup}.$$

7. The method of claim 6, comprising the steps of determining the location of the fixed reference point within the eyeball as expressed as the sum of the pupil location and the pupil-location offset:

$$x_{fixed\text{-}ref\text{-}pt}=x_{pup\text{-}loc}+x_{pup\text{-}offset}$$

$$y_{fixed\text{-}ref\text{-}pt}=y_{pup\text{-}loc}+y_{pup\text{-}offset}$$

wherein the relationships:

$x_{fixed\text{-}ref\text{-}pt}$, $y_{fixed\text{-}ref\text{-}pt}$ represent the estimated location, within the camera image, of the fixed reference point within the eyeball and $x_{pup\text{-}loc}$, $x_{pup\text{-}loc}$ represent the location of the pupil within the camera image.

8. The method of claim 2, comprising the step of estimating the pupil-center shift as a function of pupil diameter for at least two measured pupil diameter values $D_{pup}$, using the relationships:

$$x_{pup\text{-}offset}=f_x(D_{pup}), \text{ and}$$

$$y_{pup\text{-}offset}=f_y(D_{pup})$$

wherein:

$x_{pup\text{-}offset}$, $x_{pup\text{-}offset}$ are estimates of the horizontal and vertical components of the pupil center offset with respect to a fixed reference point on the eyeball;

$D_{pup}$ is a measured pupil diameter (pupil-offset feature); and $f_x(D_{pup})$, $f_y(D_{pup})$ are functions which predict the horizontal and vertical components of pupil-offset as a function of pupil diameter.

9. The method of claim 8, comprising the step of approximating the pupil-location offsets by a pair of linear equations:

$$f_x(D_{pup})=x_{nom\text{-}offset}+K_x(D_{pup}-D_{nom});$$

$$f_y(D_{pup})=y_{nom\text{-}offset}+K_y(D_{pup}-D_{nom})$$

wherein:

$D_{nom}$ is a constant representing a "nominal" pupil diameter, $x_{nom\text{-}offset}$, $y_{nom\text{-}offset}$ are constants representing the pupil-center offset given the nominal value of the pupil diameter, and $K_x$, $K_y$ are coefficients relating the change in the pupil-center offset as a function of the difference between the measured pupil diameter and the nominal pupil diameter.

10. The method of claim 9, comprising the step of determining the location of the fixed reference point within the eyeball as expressed as the sum of the pupil location and the pupil-location offset:

$$x_{fixed\text{-}ref\text{-}pt}=x_{pup\text{-}loc}+x_{pup\text{-}offset}$$

$$y_{fixed\text{-}ref\text{-}pt}=y_{pup\text{-}loc}+y_{pup\text{-}offset}$$

wherein the relationships:

$x_{fixed\text{-}ref\text{-}pt}$, $y_{fixed\text{-}ref\text{-}pt}$ represent the estimated location, within the camera image, of the fixed reference point within the eyeball and $x_{pup\text{-}loc}$, $x_{pup\text{-}loc}$ represent the location of the pupil within the camera image.

11. A method according to claim 2, comprising steps for inducing hysteresis behavior of an eye's pupil-center offset comprising the steps of:

monotonically increasing a light level from a first level to a second level;

monotonically decreasing the light level from the second level to the first level;

varying the light level in a saw tooth manner while gradually increasing and decreasing the overall light level.

12. A method according to claim 11, comprising steps for calculating the hysteresis behavior of the eye's pupil-center offset comprising the steps of:

concurrently measuring values for pupil diameter, direction of pupil-diameter change, and pupil-center location.

13. A method according to claim 11, including the steps of:

determining a prior measured pupil diameter $D_{past}$ and values for predicted pupil offset $x_{pup\text{-}offset\text{-}past}$ and $y_{pup\text{-}offset\text{-}past}$;

measuring the pupil diameter $D_{pres}$;

determining the change in pupil diameter $dD_{pup}$ with the following relationship: $dD_{pup}=D_{pres}-D_{past}$;

determining whether the pupil diameter increased or decreased;

finding appropriate values for $dx_{pup\text{-}offset}/dD_{pup}$ and $dy_{pup\text{-}offset}/dD_{pup}$ from the pupil offset hysteresis model based on at least one of the following:

pupil-diameter increase or decrease, the past pupil diameter $D_{past}$, and the past pupil offset $x_{past}$ and $y_{past}$;

computing changes in pupil offsets $dx_{pup\text{-}offset}$ and $dy_{pup\text{-}offset}$ as a function of the change in pupil diameter; and computing a quantity for new pupil offset from the old pupil offset and the change in the pupil offset with the following relationships:

$$x_{pup\text{-}offset}=x_{pup\text{-}offset\text{-}past}+dx_{pup\text{-}offset}$$

$$y_{pup\text{-}offset}=y_{pup\text{-}offset\text{-}past}+dy_{pup\text{-}offset}.$$

14. The method according to claim 11, comprising the step of computing changes in in pupil offsets $dx_{pup\text{-}offset}$ and $dy_{pup\text{-}offset}$ as a function of a change in pupil diameter, including the following steps if the pupil diameter is increasing:

$$dx_{pup\text{-}offset}=dx_{pup\text{-}offset}/dD_{pup}(D_{pup},x,\text{increasing})* dD_{pup}$$

$$dy_{pup\text{-}offset}=dy_{pup\text{-}offset}/dD_{pup}(D_{pup},y,\text{increasing})* dD_{pup};$$

and including the following steps if the pupil diameter is decreasing:

$$dx_{pup\text{-}offset}=dx_{pup\text{-}offset}/dD_{pup}(D_{pup},x,\text{decreasing})* dD_{pup}$$

$$dy_{pup\text{-}offset}=dy_{pup\text{-}offset}/dD_{pup}(D_{pup},y,\text{decreasing})* dD_{pup}.$$

15. The method of claim 14, comprising the steps of determining the location of the fixed reference point within the eyeball as expressed as the sum of the pupil location and the pupil-location offset:

$$x_{fixed\text{-}ref\text{-}pt}=x_{pup\text{-}loc}+x_{pup\text{-}offset}$$

$$y_{fixed\text{-}ref\text{-}pt}=y_{pup\text{-}loc}+y_{pup\text{-}offset}$$

wherein the relationships:

$x_{fixed\text{-}ref\text{-}pt}$, $y_{fixed\text{-}ref\text{-}pt}$ represent the estimated location, within the camera image, of the fixed reference point within the eyeball and $x_{pup\text{-}loc}$, $x_{pup\text{-}loc}$ represent the location of the pupil within the camera image.

16. A method according to claim 1, wherein the steps are performed iteratively and said step of measuring observable features of the eye includes the step of measuring a pupil diameter.

17. A method according to claim 16, comprising the step of measuring the iris/sclera boundary of the eye.

18. A method according to claim 16, comprising the step of recognizing and locating a feature of the eye from the group consisting of: a blood vessel in the sclera, a feature of the iris/pupil boundary and a mark of the iris fiber pattern in proximity of the outer edge of the iris.

19. A method of using a computer system to quantify an eye's pupil-offset behavior, comprising the following steps:

using an eyetracker system and the pupil-center-corneal reflection method to measure a first glint-pupil vector of the eye;

fixating the eye on one or more given points on a screen;

measuring at least one additional glint-pupil vector of the eye; and quantifying measured pupil offsets as functions of measured pupil diameters.

20. The method according to claim 19, comprising the step of illuminating an eye with light, varying the light level, and monitoring the eye with a video camera.

21. A method according to claim 20, further comprising the steps of accommodation for pupil-center hysteresis by:
measuring a glint-pupil vector by including measurements of pupil-center offset changes, pupil diameter changes, and determining a pupil diameter change factor as a function of whether the pupil diameter increases or decreases; and
codifying $dx_{pup\text{-}offset}/dD_{pup}$ and $dy_{pup\text{-}offset}/dD_{pup}$ expressions for at least one of a pupil-diameter-increasing case and a pupil-diameter-decreasing case.

22. The method of claim 21, comprising the steps of determining the location of the fixed reference point within the eyeball as expressed as the sum of the pupil location and the pupil-location offset:

$$x_{fixed\text{-}ref\text{-}pt} = x_{pup\text{-}loc} + x_{pup\text{-}offset}$$

$$y_{fixed\text{-}ref\text{-}pt} = y_{pup\text{-}loc} + y_{pup\text{-}offset}$$

wherein the relationships:

$x_{fixed\text{-}ref\text{-}pt}$, $y_{fixed\text{-}ref\text{-}pt}$ represent the estimated location, within the camera image, of the fixed reference point within the eyeball and $x_{pup\text{-}loc}$, $x_{pup\text{-}loc}$ represent the location of the pupil within the camera image.

23. A method according to claim 21, wherein said step of accommodating pupil-center hysteresis is performed iteratively and includes a step of measuring a pupil diameter.

24. A method according to claim 20, comprising the step of measuring the iris/sclera boundary of the eye.

25. A method according to claim 20, comprising the step of recognizing and locating a feature of the eye from the group consisting of: a blood vessel in the sclera, a feature of the iris/pupil boundary and a mark of the iris fiber pattern in proximity of the outer edge of the iris.

26. The method according to claim 20, comprising an eyetracker calibration procedure for use on a computer system wherein variations in a user's pupil diameter are stimulated by varying a light level in a viewed environment.

27. The method according to claim 20, comprising an eyetracker calibration procedure used in conjunction with a computer screen display wherein variations in the user's pupil diameter are stimulated by changing the brightness of the screen display.

28. A method according to claim 19, comprising steps for inducing hysteresis behavior of an eye's pupil-center offset comprising the steps of:
increasing a light level from a first level to a second level;
decreasing the light level from the second level to the first level;
varying the light level in a substantially saw tooth manner while gradually increasing and decreasing the overall light level.

29. A method according to claim 28, comprising steps for mapping the hysteresis behavior of an eye's pupil-center offset comprising the steps of:
concurrently measuring values for pupil diameter, direction of pupil-diameter change, and pupil-center location.

30. An apparatus for determining the location of a fixed point within an eyeball comprising:
a computer;
a camera coupled to the computer for observing the eye;
a means for measuring pupil location;
means for measuring at least one observable feature of the eye related to the relative location of the pupil within the eyeball;
a processor for estimating a pupil-location-offset with respect to a fixed point on the eyeball using the at least one measured observable eye feature; and
a processor for estimating the location of the fixed point within the eyeball as a function of the measured pupil location and the estimate of the pupil-location offset.

31. An apparatus according to claim 30, wherein the camera is a video camera that continuously observes the eye.

32. An apparatus according to claim 31, comprising:
a memory for storing a measured pupil diameter $D_{past}$ and a prior predicted pupil offset $x_{pup\text{-}offset\text{-}past}$ and $y_{pup\text{-}offset\text{-}past}$;
a processor for measuring the present pupil diameter $D_{pres}$;
a processor for determining the change in pupil diameter $dD_{pup}$, wherein $dD_{pup} = D_{pres} - D_{pas}$;
a processor for determining whether a pupil diameter increased or decreased;
a processor for finding appropriate values for $dx_{pup\text{-}offset}/dD_{pup}$ and $dy_{pup\text{-}offset}/dD_{pup}$ from the pupil offset hysteresis model based on:
pupil-diameter increase or decrease,
the past pupil diameter $D_{past}$, and
the past pupil offset $x_{past}$ and $y_{past}$;
a processor for computing the changes in pupil offset $dx_{pup\text{-}offset}$ and $dy_{pup\text{-}offset}$ as a function of the change in pupil diameter, wherein if the pupil diameter is increasing the following relations are used:

$$dx_{pup\text{-}offset} = dx_{pup\text{-}offset}/dD_{pup}(D_{pup},x,\text{increasing}) * dD_{pup};$$

$$dy_{pup\text{-}offset} = dy_{pup\text{-}offset}/dD_{pup}(D_{pup},y,\text{increasing}) * dD_{pup};$$

and, if the pupil diameter is decreasing:

$$dx_{pup\text{-}offset} = dx_{pup\text{-}offset}/dD_{pup}(D_{pup},x,\text{decreasing}) * dD_{pup}$$

$$dy_{pup\text{-}offset} = dy_{pup\text{-}offset}/dD_{pup}(D_{pup},y,\text{decreasing}) * dD_{pup}; \text{ and}$$

a processor for computing the new pupil offset from the old pupil offset and the change in the pupil offset:

$$x_{pup\text{-}offset} = x_{pup\text{-}offset\text{-}past} + dx_{pup\text{-}offset}$$

$$y_{pup\text{-}offset} = y_{pup\text{-}offset\text{-}past} + dy_{pup\text{-}offset}.$$

33. An apparatus according to claim 32, comprising a processor for performing the steps of determining the location of the fixed reference point within the eyeball as expressed as the sum of the pupil location and the pupil-location offset using the following relationships:

$$x_{fixed\text{-}ref\text{-}pt} = x_{pup\text{-}loc} + x_{pup\text{-}offset}$$

$$y_{fixed\text{-}ref\text{-}pt} = y_{pup\text{-}loc} + y_{pup\text{-}offset}$$

wherein the relationships:

$x_{fixed\text{-}ref\text{-}pt}$, $y_{fixed\text{-}ref\text{-}pt}$ represent the estimated location, within the camera image, of the fixed reference point within the eyeball and $x_{pup\text{-}loc}$, $x_{pup\text{-}loc}$ represent the location of the pupil within the camera image.

34. An apparatus according to claim 32, comprising a means for performing an eyetracker calibration subroutine for use on a computer system wherein a user's pupil diameter is measured as a light level is synchronously varied in a viewed environment.

35. An apparatus according to claim 32, further comprising an eyetracker calibration program for use in conjunction with a computer screen display wherein variations in the user's pupil diameter are measured as the pupil is stimulated by changing the brightness of the screen display.

36. A video eyetracking system comprising:
   means for measuring a pupil center location of an eyeball within a video image;
   means for estimating an offset of the pupil center location with respect to a fixed reference point on the eyeball;
   means for determining an offset-adjusted pupil-center using the offset estimate and the measured pupil center location; and
   a processor that uses the offset-adjusted pupil-center to measure the orientation of the eyeball.

37. A system as claimed in claim 36, wherein a pupil's pupil-center hysteresis is accommodated via:
   means for including measurements of pupil-center offset changes, pupil diameter changes, and a parameter for indicating whether the pupil diameter is increasing or decreasing, and
   means for codifying $dx_{pup\text{-}offset}/dD_{pup}$ and $dy_{pup\text{-}offset}/dD_{pup}$ expressions.

38. A system as claimed in claim 36, comprising:
   a medium with one or more reference points for the observer to fixate one.

39. A system according to claim 36, comprising:
   memory means for storing a plurality of measured pupil diameters $D_{past}$;
   means for recalling a prior predicted pupil offset $x_{pup\text{-}offset\text{-}past}$ and $y_{pup\text{-}offset\text{-}past}$;
   means for measuring a pupil diameter $D_{pres}$;
   means for determining a change in pupil diameter $dD_{pup}$, wherein $dD_{pup}=D_{pres}-D_{pas}$;
   means for determining whether a pupil diameter has increased or decreased;
   means for finding appropriate values for $dx_{pup\text{-}offset}/dD_{pup}$ and $dy_{pup\text{-}offset}/dD_{pup}$ from the pupil offset hysteresis model based on:
      pupil-diameter increase or decrease,
      the past pupil diameter $D_{past}$, and
      the past pupil offset $x_{past}$ and $y_{past}$;
   means for computing changes in pupil offsets $dx_{pup\text{-}offset}$ and $dy_{pup\text{-}offset}$ as a function of a change in pupil diameter, wherein if the pupil diameter is increasing the following relations are used:

$$dx_{pup\text{-}offset}=dx_{pup\text{-}offset}/dD_{pup}(D_{pup},x,\text{increasing})* dD_{pup}$$

$$dy_{pup\text{-}offset}=dy_{pup\text{-}offset}/dD_{pup}(D_{pup},y,\text{increasing})* dD_{pup};$$

and, if the pupil diameter is decreasing:

$$dx_{pup\text{-}offset}=dx_{pup\text{-}offset}/dD_{pup}(D_{pup},x,\text{decreasing})* dD_{pup}$$

$$dy_{pup\text{-}offset}=dy_{pup\text{-}offset}/dD_{pup}(D_{pup},y,\text{decreasing})* dD_{pup};$$ and means for computing pupil offset values using the relationships:

$$x_{pup\text{-}offset}=x_{pup\text{-}offset\text{-}past}+dx_{pup\text{-}offset}$$

$$y_{pup\text{-}offset}=y_{pup\text{-}offset\text{-}past}+dy_{pup\text{-}offset}.$$

40. A system according to claim 39, comprising a means for performing an eyetracker calibration subroutine for use on a computer system wherein a user's pupil diameter is measured as a light level is synchronously varied with the measurements.

41. A system according to claim 39, comprising an eyetracker calibration on a programmable chip for use in conjunction with a computer screen display wherein variations in the user's pupil diameter are measured as the pupil is stimulated by changing the brightness of a screen display.

42. A system according to claim 39, comprising means for determining the location of a fixed reference point within an eyeball as expressed as the sum of the pupil location and the pupil-location offset using at least the following relationships:

$$x_{fixed\text{-}ref\text{-}pt}=x_{pup\text{-}loc}+x_{pup\text{-}offset}$$

$$y_{fixed\text{-}ref\text{-}pt}=y_{pup\text{-}loc}+y_{pup\text{-}offset}$$

wherein the relationships:
   $x_{fixed\text{-}ref\text{-}pt}$, $y_{fixed\text{-}ref\text{-}pt}$ represent the estimated location, within the camera image, of the fixed reference point within the eyeball and $x_{pup\text{-}loc}$, $x_{pup\text{-}loc}$ represent the location of the pupil within the camera image.

43. A system according to claim 36, comprising a means for performing an eyetracker calibration subroutine for use on a computer system wherein a user's pupil diameter is measured as a light level is synchronously varied in a viewed environment.

44. A system according to claim 36, comprising a programmable eyetracker calibration subroutine for use on a computer system in conjunction with a computer screen display wherein variations in the user's pupil diameter are measured as the pupil is stimulated by changing the brightness of a screen display.

* * * * *